(12) United States Patent
Ahn et al.

(10) Patent No.: US 7,579,460 B2
(45) Date of Patent: Aug. 25, 2009

(54) METHOD FOR TAGGING OF CARBOHYDRATES WITH ACTIVE METHYLENE COMPOUND

(75) Inventors: Yeong Hee Ahn, Cheongju-shi (KR); Jong Shin Yoo, Daejeon-shi (KR); Soohyun Kim, Daejeon-shi (KR)

(73) Assignee: Korea Basic Science Institute, Daejeon (KR)

( * ) Notice: Subject to any disclaimer, the term of this patent is extended or adjusted under 35 U.S.C. 154(b) by 0 days.

(21) Appl. No.: 11/307,457

(22) Filed: Feb. 8, 2006

(65) Prior Publication Data

US 2007/0185316 A1    Aug. 9, 2007

(51) Int. Cl.
| | |
|---|---|
| C08B 37/08 | (2006.01) |
| C07B 37/10 | (2006.01) |
| C07B 37/00 | (2006.01) |
| C07H 3/06 | (2006.01) |

(52) U.S. Cl. .................. 536/55.1; 536/55; 536/55.2; 536/55.3; 536/123; 536/123.1

(58) Field of Classification Search .................. 514/33
See application file for complete search history.

(56) References Cited

OTHER PUBLICATIONS

Ahn et. al. Analytical Sciences, Jul. 2001, (17), 893-895.*
Carey and Sundberg, Advanced Organic Chemistry, 3rd Edition, 1993, pp. 128-130.*
Sears et. al., Science, 291, 2001, 2344-2350.*
Dell et. al., Science, 291, 2001, 2351-2356.*
Cramer et al., "A Reversed-Phase Ion-Pair High-Performance Liquid Chromatography Method for Bovine Testicular Hyaluronidase Digests Using Postcolumn Derivitization with 2-Cyanoacetamide and Ultraviolet Detection" Analytical Biochemistry (1991) vol. 196 pp. 183-189.*
Rothenberg et al, "Biotinylated diaminopyridine: An approach to tagging oligosaccharides and exploring their biology", Proc. Natl. Acad. Sci. USA (1993), 90: 11939-11943.
Liu et al, "Ultrasensitive fluorometric detection of carbohydrates as derivatives in mixtures separated by capillary electrophoresis", Proc. Natl. Acad. Sci. USA (1991), 88: 2302-2306.
Suzuki et al, "Analysis of 1-Aminopyrene-3, 6, 8-trisulfonate-Derivatized Oligosaccharides by Capillary Electrophoresis with Matrix-Assisted Laser Desorption/Ionization Time-of Flight Mass Spectrometry", Anal. Chem. (1997), 69: 4554-4559.
Monsarrat et al, "Characterization of mannooligosaccharide caps in mycobacterial lipoarabinomannan by capillary electrophoresis/ electrospray mass spectrometry", Glycobiology (1999), 9(4): 335-342.
Ramsay et al, "Mild tagging procedures for the structural analysis of glycans", Carbohydrate Research (2001), 333:59-71.
Hase, "Precolumn derivatization for chromatographic and electrophoretic analyses of carbohydrates", Journal of Chromatography A (1996), 720: 173-182.
Bigge et al, "Nonselective and Efficient Fluorescent Labeling of Glycans Using 2-Amino Benzamide and Anthranilic Acid", Analytical Biochemistry (1995), 230: 229-238.
Eger et al., "The First Condensation Product of Malononitrile with Ribose," Liebigs Ann. Chem., (1989) p. 1049.
Zinner et al., "Die Kondensation von 2.3;4.5-Diisopropyliden-al-D-arabinose mit Verbindungen, die aktive Methylengruppen enthalten," Chemische Berichte, (1959) vol. 92:1614-1617.
Lopez Aparicio et al., "Some Applications of the Knoevenagel Reaction in the Carbohydrate Field," Carbodydrate Research, (1979) 69:55-70.
Lopez Aparicio et al., "Loss or transfer of an acetyl group during Knoevenagel reactions of aldehydo sugars with acetylacetone," Carbohydrate Research, (1985)135:303-311.
Tadano et al., "A Novel Transformation of Four Aldoses to Some Optically Pure Pseudohexopyranoses and a Pseudopentofuranose . . . ," J. Org. Chem., (1987) 52:1946-1956.
Breuer et al., "Antiviral Compounds. a. Structure-Activity Relationship of Some Antiviral Enediones Derived from Aldehydo Sugars," J. Med. Chem., (1983) 26:30-34.
Ahn and Yoo, "Piperidine as an Efficient Organic Catalyst of Derivatization of Oligosaccharides with Malononitrile for High-Sensitivity Electrospray Ionization Mass Analysis," Analytical Sciences, (2001) 17:893-895.
Lamari et al., "Derivatization of carbohydrates for chromatographic, electrophoretic and mass spectrometric structure analysis," J. Chromatography B, (2003) 793(1):15-36.
Tietze and Beifuss, "The Knoevenagel Reaction," Comprehensive Organic Chemistry, (1991) 2:341-394.

* cited by examiner

*Primary Examiner*—Shaojia Anna Jiang
*Assistant Examiner*—Eric S Olson
(74) *Attorney, Agent, or Firm*—Joseph Hyosuk Kim; JHK Law

(57) ABSTRACT

The present invention relates to the method for tagging of carbohydrates with active methylene compound. Particularly, it relates to the method for tagging of carbohydrates with active methylene compound comprising the step of preparing carbohydrate conjugate in which carbohydrate and methylene compound are combined by mixing carbohydrate mixture and methylene compound under aqueous polar aprotic solvent containing amine base catalyst. The tagging method of the present invention does not need many kinds of chemical reagent and the reactions can be taken even in the presence of certain amount of impurities. So, it can be used for the analysis of oligosaccharide present in the various kinds of samples.

9 Claims, 3 Drawing Sheets

METHOD FOR TAGGING OF CARBOHYDRATES WITH ACTIVE METHYLENE COMPOUND

FIELD OF THE INVENTION

The present invention relates to a method for tagging of carbohydrates with active methylene compound. Particularly, it relates to the method for tagging of carbohydrates with active methylene compound comprising the step of preparing carbohydrate conjugate in which carbohydrate and methylene compound are combined by mixing carbohydrate mixture and methylene compound under aqueous polar aprotic solvent containing amine base catalyst.

BACKGROUND

It is well recognized that oligosaccharides have a variety of biologically important roles either as free carbohydrates or as constituents of glycoconjugates. In plants free oligosaccharides play important roles in carbon fluxes within the cells and as a regulator. Oligosaccharides bonded to proteins also influence protein stability, folding, and biological functions of glycoproteins. Intercellular recognition by proteins may be affected by the structure and nature of oligosaccharides. Thus the characterization of complex oligosaccharides obtained from a variety of biological media has become of increased importance, involving many kinds of analytical techniques.

Unfortunately due to the restricted amount and complexity of samples obtained from biological media and the low proton affinity of oligosaccharides, there are many problems to be solved for the effective purification and the sensitive detection of oligosaccharides. In order to improve the sensitivity and the detectable mass range of oligosaccharides, derivatization methods such as reductive amination, designed to form a covalent bond with a variety of ligands containing nitrogen atoms, were introduced.

By the reductive amination method, the detection limit of derivatized oligosaccharides was improved greatly to fmol levels. But prior to analysis of the sample derivatized by this method, a purification procedure for the removal of excess reagents, such as sodium cyanoborohydride and the non-volatile organic ligand used, is necessary. This procedure sometimes is tedious and can be problematic especially in cases where restricted amounts of sample are available.

Therefore, for more convenient and low-level detection of oligosaccarides without pre-treatment of sample, the development of new derivatization methods for oligosaccharides is desirable.

SUMMARY OF THE INVENTION

The present invention provides a method for tagging of carbohydrates with active methylene compound comprising the step of producing carbohydrate-tagged conjugate wherein carbohydrate is bonded with methylene compound by mixing carbohydrate mixtures with active methylene compound under aqueous aprotic solvents containing amine base catalyst.

In the above method, aldol adduct is formed by the addition reaction between hemicaetal (aldehyde) group of carbohydrate moiety and carbon nucleophile (enolate) of active methylene compound, following elimination of water from the resulting aldol adduct to form α,β-unsaturated carbohydrate-tagged conjugates. The resulting α,β-unsaturated carbohydrate-tagged conjugate is converted to its ring closure form wherein sugar ring is formed by the conjugate addition of hydroxyl group in the carbohydrate chain under the basic conditions. In the method of the present invention, tagging reaction can be taken under the conditions, wherein many hydroxyl groups present in the carbohydrate chain of oligosaccharides are not protected. Active methylene compound playing as a carbon nucleophile can be malononitrile, alkyl malonate, α-cyanomalonate, β-ketoester etc. or the counterparts thereof bound to macromolecule. The tagging reaction can be carried under aqueous basic condition using inorganic base or under polar aprotic solvent, such as DMF, NMP, DMSO etc., containing a portion of water and an amine base as a mild organic base catalyst. In the preferred embodiment of the present invention, method for the tagging of carbohydrates with active methylene compound and for the purification of the tagged oligosaccharides using such as carbohydrate affinity membrane or chromatographic techniques are disclosed.

DETAILED DESCRIPTION OF PREFERRED EMBODIMENTS

The present invention relates to the method for tagging of carbohydrates with active methylene compound comprising the step of preparing carbohydrate conjugate in which carbohydrate and methylene compound are combined by mixing carbohydrate mixture and methylene compound under aqueous polar aprotic solvent containing amine base catalyst.

In the present invention, active methylene compound has the characteristics having two carbanion-stabilizing groups composed of carbonyl and/or nitrile group which can stabilize α-carbanion functioning as a nucleophile such as malononitrile, alkyl malonate, α-cyanoacetate, β-ketoester, β-ketoamide etc, and is preferred to have the structure of Chemical Formula 1. (F. Carey and R. Sundberg, "Advanced Organic Chemistry, Part B: Reactions and Synthesis, $3^{rd}$ ed., Plenum Press, p. 83-85).

<Chemical Formula 1>

X and/or Y: CN, —CO—, —COO—, —CONH—

In the preferred embodiment of the present invention, malononitrile was used as an active methylene compound. In addition, active methylene compound can be selected from counterparts of polymers wherein each of them is bound to the solid support.

In the tagging method of the present invention, amine base catalyst can preferably be selected from a group consisting of piperidine, pyridine, pyrrolidine, sarcosine and simple amineacid. Among them, piperidine is more preferable.

In addition, polar aprotic solvent can preferably be selected from a group consisting of dimethylformamide, dimethylsulfoxide, N-methylpyrrolidinone, N-methylpiperidone and dimethoxyethane. Among them, dimethylformamide is more preferable.

In addition, carbohydrate can be selected from a group consisting of N-linked oligosaccharide and O-linked oligosaccharide of glycoprotein, and unprotected oligosaccharide having free hydroxy group at the sugar backbone is more preferable.

Carbohydrate conjugate tagged with active methylene compound prepared by the tagging method of the present invention can be purified by various purifying and analyzing methods known to the persons skilled in the art without any limitations. Said various purifying and analyzing methods can be selected from a group consisting of the method using ion exchange resin, the gel filtration method, the method using carbohydrate affinity matrix, the method using various kinds of chemically bound stationary phase and the method using adsorption medium, and the method using carbohydrate affinity matrix is more preferable for the rapid separation. In addition, aminoalkyl is preferable as a stationary phase in the chemically bound stationary phase chromatography.

By the above method, conjugate in which carbon-carbon bond is formed between reducing end of carbohydrate and active methylene carbon moiety of the active methylene compound can preferably be produced.

Figure 1:
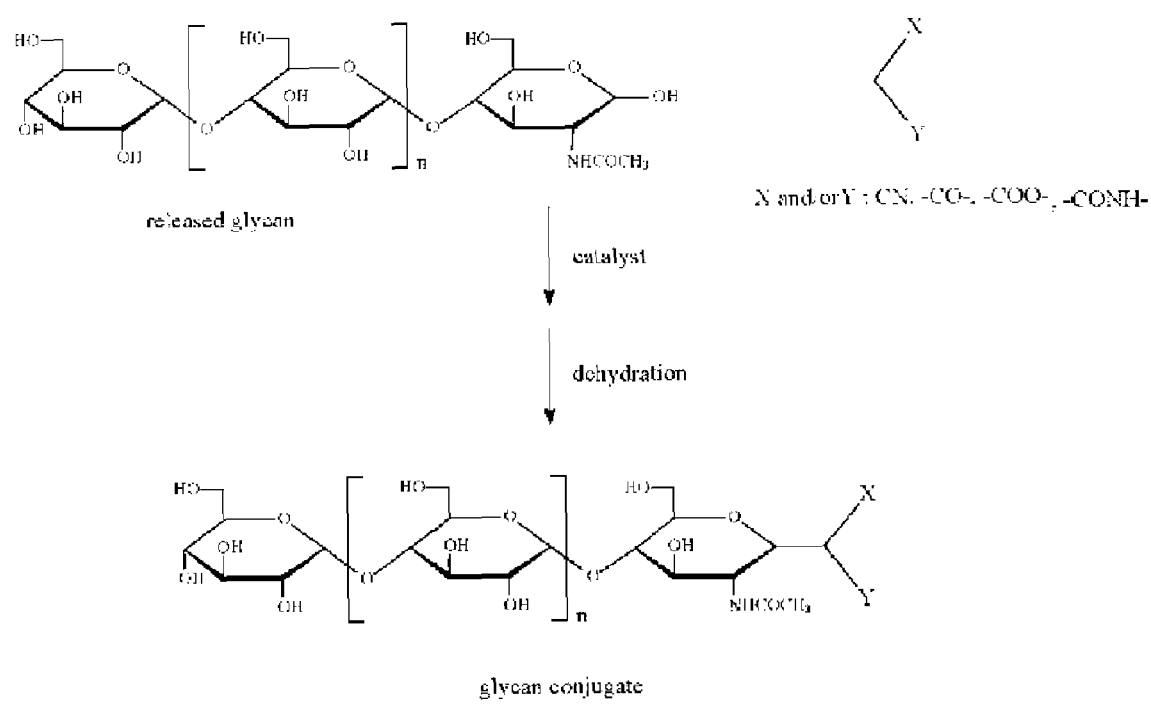
FIG. 1 is a schematic representation of the oligosaccharide derivatives tagged with active methylene compound of the present invention.

The present invention relates to a mild and efficient tagging method of oligosaccharide, mainly O-linked or N-linked, obtained from biological medium (see FIG. 1). Oligosaccharide obtained from biological medium is generally having many free hydroxyl groups on sugar backbone and restrict in the amount. Therefore, it is necessary to develop an efficient and simple tagging method without protection of many hydroxyl groups of oligosaccharide for separation and structural analysis of biologically active oligosaccharide for the use of diagnostic and industrial application.

The hemiacetal group at the reducing end of oligosaccharide is a synthetic equivalent of aldehyde. This group can react with an active methylene donor, such as malononitrile, to afford the conjugated derivative of the oligosaccharide through an addition and elimination reaction. Such an addition and elimination reaction of an simple aldehyde with an active methylene donor in anhydrous condition is known as the aldol condensation and dehydration reaction, and is a well known synthetic method in the field of organic chemistry. For efficient tagging of oligosaccharides having many free hydroxyl groups with an active methylene compound, however, aqueous conditions are inevitably necessary because of solubility of sugar. Moreover, the chemical reactivity at the reducing end of oligosaccharide can be greatly different with respect to the kind of sugar moieties present in the reducing end. For example, maltooligosaccharides having glucose unit at the reducing end of sugar chain can readily react with carbon nucleophile in aqueous basic condition. But N-acetylglucosamine terminal moiety often observed in oligosaccharides released from glycoprotein of biological media shows much less reactivity for carbon nucleophile used in the case of maltooligosaccharides, making tagging reaction to be hardly proceeded. A tagging method of free oligosaccharides, having N-acetylglucosamine as a reducing sugar moiety and unprotected many hydroxyl groups on sugar backbone, with active methylene compound as a carbon nucleophile, is described in the present invention.

In the preferred embodiment of the present invention, $Man_5NAcGlu_2$, as a typical oligosaccharide, is mixed with the DMF solution of malononitrile, as a representative tagging agent. To this reaction solution was added excess neat piperidine as a base and an amine catalyst. The solvent composition can be varied, but exceedingly increased portion of water can retard the progress of tagging reaction. Among several amines being exploitable as a catalyst for easy formation of Schiff base and/or as a base for inauguration of enolate formation of nucleophile, piperidine can be preferably selected. In the preferred embodiment of the present invention, the reaction tube was shaken for several seconds then incubated at temperature ranging from 4° C. to 40° C. The reaction rate is affected from the kind of reducing end moiety of oligosaccharide and reaction conditions such as the composition of solvent, concentration of the samples, aliquot of the catalyst and temperature, etc.

The reaction can be analyzed by matrix assisted laser desorption/ionization mass spectrometry (MALDI-MS), which is one of the powerful analytical tools for carbohydrate oligomer, having a high sensitive detectability to even impure sample. DHBA as a matrix compound can be used for the sensitive detection of the oligosaccharide-malononitrile derivative and free oligosaccharide. All signals of molecular ions obtained in this invention can be recorded as sodium ion adducts. Although several peaks due to minor impurities could also be detected, the present inventors could assign the peaks due to interesting components in the derivatization mixture (See FIG. 2 and FIG. 3).

The malononitrile tagging method can also be applied to the tagging for multi-component oligosaccharides. Oligosaccharide mixture, released from a glycoprotein is nicely tagged following the method of the present invention (See FIG. 3). The progression of the tagging reaction can be detected easily using MALDI-TOF MS. For analysis of oligosaccharides obtained from biological media, more flexible tagging condition is normally need since the purity and concentration of these sample can be variable drastically. The method of the present invention is tolerable from impurities present in sample in a wide range. The method of the present invention is also tolerable in a wide range of usage of tagging reagents from $10^2$ equivalent to $10^4$ equivalent, and give reproducible results in the range. Additionally, the malononitrile derivative of an oligosaccharide has a highly ionizable proton at the opposition to the carbonyl or nitrile group. It has been reported that the derivatives of oligosaccharide with an active methylene compound show a high sensitivity in negative electrospray ionization (ESI) mode mass analysis.

In the second point of the present invention, the present invention provides the method for the purification of oligosaccharides tagged by active methylene compound. For tagging of a restricted amount of biological samples, excess reagent is generally used for completion of reaction or for convenience of experiment. Thus effective purification process is very important in applying the tagging method to a variety of purpose.

Although tagged oligosaccharide derivatives of the present invention have a tag moiety less polar than native oligosaccharides, they are still highly hydrophilic by virtue of oligosaccharide moiety of the tagged derivative having many hydroxy group on sugar chain. In contrast, all reagents used for the tagging reaction of oligosaccharide are non-ionic organic materials except water used as a solvent. Any kind of inorganic reagent is not required for the tagging reaction of oligosaccharide in the present invention. Thus affinity purification method exploiting the hydrophilic property due to sugar moiety of tagged samples is plausible. As an example representative, cellulose filter kit can be used for simple purification of tagged sugar. After the cellulose filter kit activated by aqueous acetic acid solution is equilibrated with acetonitrile, a portion of reaction solution is loaded on filter and equilibrated for a few minutes. Chemical reagents to be removed, such as polar aprotic organic solvents, tagging reagent and organic amine base catalysts, are washed off by a water miscible organic solvent or aqueous mixture thereof. Tagged oligosaccharide purified can be eluted with water. When active methylene compound bound to polymer or solid support is used as a tagging compound, the purification process of solid-bound tagged sugar can also be conducted simply by washing techniques with an appropriate solvent.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1

Tagging of Oligosaccharide

N-linked oligosaccharide mixture obtained from glycoproteins present in the biological media by a known biological or chemical method of the prior art was dissolved in 2 µl distilled water. Malononitrile (1.0 µmol, 66 µg) was dissolved in dimethylformamide (10 µl) and was mixed with aqueous oligosaccharide solution prepared above. After piperidine (1.0 µmol, 0.1 µl) was added to the above tagging solution, the reaction tube was incubated at low temperature (10° C.-15° C.) for about 3 days. A portion of tagging solution was taken and purified.

Example 2

Purification of the Tagged Oligosaccharide

A cellulose filter was activated through washing with 5 ml of water and subsequent 30% aqueous acetic acid solution. A portion of the tagging solution of oligosaccharides prepared by the method of Example 1 was loaded onto the filter. After standing for about 10 min, the filter was washed with 5 ml of anhydrous acetonitrile. The tagged oligosaccharides was eluted from the filter with water (0.5 ml×2) and was dried under vacuum. After dissolving lyophilized tagged oligosaccharide into distilled water, some of them were taken for MALDI MS (matrix assisted laser desorption/ionization mass spectrosmatry) analysis. DHBA (dihydroxybenzoic acid) was uses as a matrix.

Figure 2:
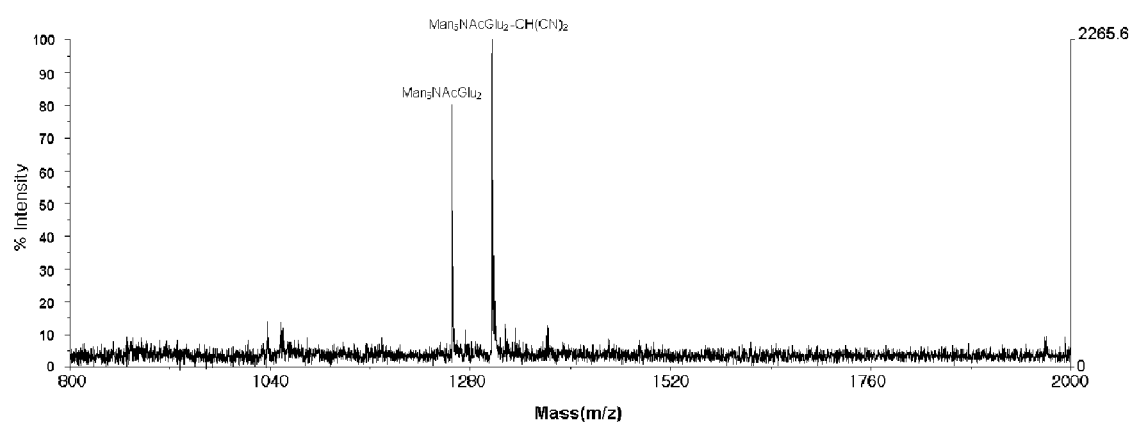
FIG. 2 is a Positive-ion MALDI-TOF MS spectrum obtained from the partially tagged oligosaccharide ($Man_5NAcGlu_2$) with one of the active methylene moiety, malononitrile.
Figure 3:
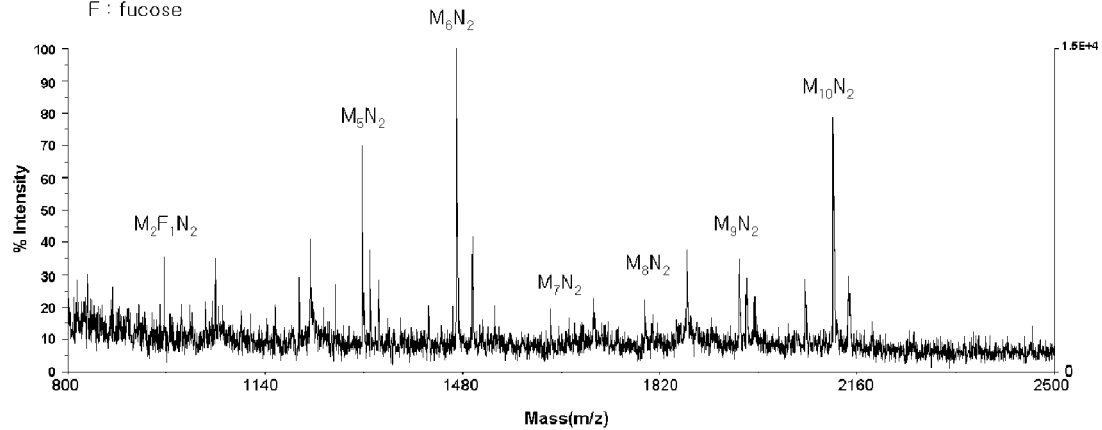
FIG. 3 is Positive-ion MALDI-TOF MS spectrum obtained from the N-linked oligosaccharide mixture tagged fully with one of the active methylene moiety, malononitrile.

As a result, all the mass spectral signals of sample compound were recorded as a sodium ion adduct (FIG. 2 and FIG. 3).

INDUSTRIAL APPLICABILITY

As described hereinbefore, the tagging method of the present invention does not need many kinds of chemical reagent and the reactions can be taken even in the presence of certain amount of impurities. So, it can be used for the analysis of oligosaccharide present in the various kinds of samples.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for tagging a carbohydrate, selected from an N-linked oligosaccharide and an O-linked oligosaccharide of a glycoprotein with N-acetylglucosamine as a reducing sugar moiety and unprotected hydroxyl groups in the sugar backbone, with an active methylene compound with two carbanion-stabilizing groups composed of carbonyl and/or nitrile group, said method comprising preparing a α, β-unsaturated carbohydrate-tagged conjugate that converts to ring closure form by the conjugate addition to hydroxyl group in the carbohydrate chain under basic conditions in which the carbohydrate and the methylene compound are combined by mixing carbohydrate mixture and the methylene compound under aqueous polar aprotic solvent containing amine base catalyst, whereby an elimination and addition reaction between the carbohydrate and the methylene compound is carried out.

2. The method according to claim 1, wherein the carbohydrate conjugate is produced by the carbon-carbon bond formation between reducing end of carbohydrate and active methylene carbon of the active methylene compound.

3. The method according to claim 1, wherein the amine base catalyst is selected from piperidine, pyridine, pyrrolidine, sarcosine and simple amineacid.

4. The method according to claim 3, wherein the amine base catalyst is piperidine.

5. The method according to claim 1, wherein the polar aprotic solvent is selected from dimethylformamide, dimethylsulfoxide, N-methylpyrrolidinone, N-methylpiperidone and dimethoxyethane.

6. The method according to claim 5, wherein the polar aprotic solvent is dimethylformamide.

7. The method according to claim 1, wherein the active methylene compound is selected from a group consisting of malononitrile, alkyl malonate, α-cyanoacetate, α-cyanoacetamide, β-ketoester, β-ketoamide and derivatives thereof bound to a polymer or a solid support.

8. The method according to claim 7, wherein the active methylene compound is malononitrile.

9. The method according to claim 1, wherein the active methylene compound has the structure of Formula I:

wherein X and/or Y is —CN, —COR, —COOR, or —CONHR where R is H or alkyl.

* * * * *